United States Patent
Sang et al.

(10) Patent No.: US 11,786,216 B2
(45) Date of Patent: Oct. 17, 2023

(54) ULTRASOUND CONTRAST ENHANCED IMAGING METHOD AND ULTRASOUND IMAGING SYSTEM

(71) Applicants: SHENZHEN MINDRAY BIO-MEDICAL ELECTRONICS CO., LTD., Guangdong (CN); BEIJING SHEN MINDRAY MEDICAL ELECTRONICS TECHNOLOGY ACADEMY CO., LTD., Beijing (CN)

(72) Inventors: Maodong Sang, Beijing (CN); Xirui Zhang, Beijing (CN); Lei Zhu, Beijing (CN)

(73) Assignees: Shenzhen Mindray Bio-Medical Electronics Co., Ltd., Shenzhen (CN); Beijing Shen Mindray Medical Electronics Technology Academy Co., Ltd., Beijing (CN)

( * ) Notice: Subject to any disclaimer, the term of this patent is extended or adjusted under 35 U.S.C. 154(b) by 130 days.

(21) Appl. No.: 16/874,553

(22) Filed: May 14, 2020

(65) Prior Publication Data
US 2020/0268352 A1 Aug. 27, 2020

Related U.S. Application Data

(63) Continuation of application No. PCT/CN2017/111898, filed on Nov. 20, 2017.

(51) Int. Cl.
*A61B 8/08* (2006.01)
*A61B 8/00* (2006.01)

(52) U.S. Cl.
CPC .............. *A61B 8/481* (2013.01); *A61B 8/461* (2013.01); *A61B 8/5207* (2013.01); *A61B 8/5215* (2013.01)

(58) Field of Classification Search
CPC ......... A61B 8/461; A61B 8/463; A61B 8/481; A61B 8/5207; A61B 8/5215;
(Continued)

(56) References Cited

U.S. PATENT DOCUMENTS

| | | | | |
|---|---|---|---|---|
| 5,928,151 A * | 7/1999 | Hossack | ............ | G01S 15/8993 600/443 |
| 2001/0025143 A1 * | 9/2001 | Suzuki | ................ | G01S 15/8981 600/458 |

(Continued)

FOREIGN PATENT DOCUMENTS

| CN | 104739448 A | 7/2015 |
|---|---|---|
| CN | 106102588 A | 11/2016 |

(Continued)

OTHER PUBLICATIONS

Soren K. Jespersen et al., "Multi-Angle Compound Imaging," Apr. 1, 1998, Ultrasonic Imaging, 20, pp. 81-102 (Year: 1998).*

(Continued)

*Primary Examiner* — Joseph M Santos Rodriguez
*Assistant Examiner* — Maria Christina Talty
(74) *Attorney, Agent, or Firm* — Sheppard Mullin Richter & Hampton LLP

(57) ABSTRACT

Disclosed in the present application is an ultrasound contrast enhanced imaging method, comprising: transmitting unfocused waves in a plurality of angles to a target region containing microbubbles; receiving echo signals of the unfocused waves; selecting echo signals corresponding to at least some of the plurality of angles from the echo signals; generating contrast enhanced image according to the selected echo signals, performing color-coding on the contrast enhanced image, and displaying same. Also disclosed in the present application is an ultrasound imaging system.

15 Claims, 4 Drawing Sheets

(58) Field of Classification Search
CPC ............... A61B 8/5253; G01S 15/8981; G01S 15/8995; G01S 7/52039; G01S 7/52071
See application file for complete search history.

(56) References Cited

U.S. PATENT DOCUMENTS

| | | | | |
|---|---|---|---|---|
| 2003/0073903 | A1* | 4/2003 | Sato | A61B 8/461 600/443 |
| 2010/0312113 | A1* | 12/2010 | Ogasawara | A61B 8/481 600/443 |
| 2015/0324957 | A1* | 11/2015 | Honjo | A61B 8/54 600/447 |

FOREIGN PATENT DOCUMENTS

| | | |
|---|---|---|
| CN | 106580369 A | 4/2017 |
| CN | 106725599 A | 5/2017 |
| CN | 106971055 A | 7/2017 |
| WO | 02-19912 A2 | 3/2002 |
| WO | 2004/110279 A1 | 12/2004 |

OTHER PUBLICATIONS

Olivier Couture et al., "Ultrasound Contrast Plane Wave Imaging," IEEE Transactions on Ultrasonics, Ferroelectrics, and Frequency Control, Dec. 2012, vol. 59, No. 12 (Year: 2012).*

PCT International Search Report and the Written Opinion dated Aug. 9, 2018, issued in related International Application No. PCT/CN2017/111898, with partial English translation (10 pages).

Xirui Zhang et al., "Review on State-of-the-Art of Contrast-Enhanced Ultrasound Imaging", Chinese Journal of Biomedical Engineering, vol. 35, No. 2, Apr. 2016, pp. 225-233 (with English language abstract).

PCT International Preliminary Report on Patentability dated Jun. 4, 2020, issued in related International Application No. PCT/CN2017/111898, with English translation (10 pages).

First Search dated Jul. 5, 2020, issued in related Chinese Application No. 201780017836.4 (1 page).

First Office Action dated Jul. 9, 2020, issued in related Chinese Application No. 201780017836.4, with English machine translation (12 pages).

* cited by examiner

ULTRASOUND CONTRAST ENHANCED IMAGING METHOD AND ULTRASOUND IMAGING SYSTEM

CROSS REFERENCE TO RELATED APPLICATION

This application is a continuation application of International Application No. PCT/CN2017/111898, filed on Nov. 20, 2017, the contents of which is incorporated herein by reference in its entirety in the present disclosure.

TECHNICAL FIELD

The present disclosure relates to an ultrasound imaging method, in particular to a contrast enhanced ultrasound imaging method and an ultrasound imaging system using the contrast enhanced ultrasound imaging method.

BACKGROUND

Ultrasound contrast agent microbubbles can enhance the strength of the echoes. The ultrasound contrast agent microbubbles have very small diameters which are similar to blood cells, and can diffuse to various organs of the human body with the blood. Moreover, the movement of the contrast agent microbubbles has significant nonlinear characteristics. With the maturity of contrast enhanced ultrasound imaging technology based on non-linear characteristics, the contrast enhanced ultrasound imaging has been widely used in the benign and malignant identification, diagnosis and treatment of tumors. Since the contrast agent diffuses with the blood, the velocity of the contrast agent microbubbles observed on the ultrasound contrast enhanced image can represent the blood flow velocity in the section to some extent. However, in the existing contrast enhanced imaging based on line-by-line scanning, in addition to the shortcomings of low frame rate, the image can only show the difference in microbubble intensity, but the difference in the velocities of the contrast agent microbubbles in the section cannot be visually displayed. The doctor can only make subjective judgment according to the change of the frames by experience, but cannot accurately determine the velocities of the contrast agent microbubbles through the ultrasound contrast enhanced image.

SUMMARY

Therefore, in embodiments of the present disclosure, contrast enhanced ultrasound imaging methods and ultrasound imaging systems using such contrast enhanced ultrasound imaging methods are provided, which can distinguish and display the contrast microbubbles with different velocities.

In one embodiment, a contrast enhanced ultrasound imaging method is provided, which may include: transmitting unfocused waves to the a target region containing microbubbles in multiple angles; receiving echo signals of the unfocused waves transmitted in the multiple angles; selecting echo signals corresponding to at least a part of the multiple angles from the echo signals of the unfocused waves transmitted in the multiple angles; generating contrast enhanced images according to the selected echo signals; color-coding the contrast enhanced images; and displaying the color-coded contrast enhanced images.

In one embodiment, selecting the echo signals corresponding to the at least a part of the multiple angles from the echo signals of the unfocused waves transmitted in the multiple angles may include: selecting echo signals corresponding to a first number of angles from the echo signals of the unfocused waves transmitted in the multiple angles to obtain a first group of selected echo signals; and selecting echo signals corresponding to a second number of angles from the echo signals of the unfocused waves transmitted in the multiple angles to obtain a second group of selected echo signals. Generating the contrast enhanced images according to the selected echo signals may include: generating a first group of contrast enhanced image according to the first group of selected echo signals; and generating a second group of contrast enhanced image according to the second group of selected echo signals. The first number may be greater than the second number.

In one embodiment, color-coding the contrast enhanced image may include color-coding the first group of contrast enhanced image with a first color and color-coding the second group of contrast enhanced image with a second color. The first color may be different from the second color.

In one embodiment, color-coding the contrast enhanced image may include color-coding the first group of contrast enhanced image with a first color and color-coding the second group of contrast enhanced image with a second color. The first color and the second color may be a same color and have different transparencies.

In one embodiment, displaying the color-coded contrast enhanced image may include combining the first group of contrast enhanced image and the second group of contrast enhanced image to obtain a combined contrast enhanced image and displaying the combined contrast enhanced image.

In one embodiment, generating the first group of contrast enhanced image according to the first group of selected echo signals may include: performing a coherent compound processing on the first group of selected echo signals; extracting nonlinear signals from the first group of selected echo signals on which the coherent compound processing has been performed; and generating the first group of contrast enhanced image according to the nonlinear signals extracted from the first group of selected echo signals on which the coherent compound processing has been performed. Generating the second group of contrast enhanced image according to the second group of selected echo signals may include: performing a coherent compound processing on the second group of selected echo signals; extracting nonlinear signals from the second group of selected echo signals on which the coherent compound processing has been performed; and generating the second group of contrast enhanced image according to the nonlinear signals extracted from the second group of selected echo signals on which the coherent compound processing has been performed.

In one embodiment, the unfocused waves may be plane waves.

In one embodiment, an ultrasound imaging system is provided, which may include: a transducer; a transmitting circuit which excites the transducer to transmit unfocused waves to a target region containing microbubbles in multiple angles; a receiving circuit which receives echo signals of the unfocused waves transmitted in the multiple angles through the transducer; a processor which selects echo signals corresponding to at least a part of the multiple angles from the echo signals of the unfocused waves transmitted in the multiple angles, generates contrast enhanced images according to the selected echo signals and color-codes the contrast enhanced images; and a display device which displays the color-coded contrast enhanced images.

In one embodiment, the processor may: select echo signals corresponding to a first number of angles from the echo signals of the unfocused waves transmitted in the multiple angles to obtain a first group of selected echo signals; selects echo signals corresponding to a second number of angles from the echo signals of the unfocused waves transmitted in the multiple angles to obtain a second group of selected echo signals; generates a first group of contrast enhanced image according to the first group of selected echo signals; and generates a second group of contrast enhanced image according to the second group of selected echo signals. The first number may be greater than the second number.

In one embodiment, the processor may color-code the first group of contrast enhanced image with a first color and color-code the second group of contrast enhanced image with a second color, where the first color may be different from the second color.

In one embodiment, the processor may color-code the first group of contrast enhanced image with a first color and color-code the second group of contrast enhanced image with a second color, where the first color and the second color may be a same color and have different transparencies.

In one embodiment, the processor may combine the first group of contrast enhanced image and the second group of contrast enhanced image to obtain a combined contrast enhanced image, and the display device may display the combined contrast enhanced image.

In one embodiment, the processor may perform a coherent compound processing on the first group of selected echo signals and extract nonlinear signals from the first group of selected echo signals on which the coherent compound processing has been performed to generate the first group of contrast enhanced image, and perform a coherent compound processing on the second group of selected echo signals and extracts nonlinear signals from the second group of selected echo signals on which the coherent compound processing has been performed to generate the second group of contrast enhanced image.

In one embodiment, an ultrasound imaging system is provided, which may include: a transducer; a transmitting circuit which excites the transducer to transmit unfocused waves to a target region containing microbubbles in multiple angles; a receiving circuit which receives echo signals of the unfocused waves transmitted in the multiple angles through the transducer; a processor which selects echo signals corresponding to a first number of angles in the multiple angles from the echo signals of the unfocused waves transmitted in the multiple angles to obtain a first group of selected echo signals, selects echo signals corresponding to a second number of angles in the multiple angles from the echo signals of the unfocused waves transmitted in the multiple angles to obtain a second group of selected echo signals, generates a first group of contrast enhanced image according to the first group of selected echo signals, generates a second group of contrast enhanced image according to the second group of selected echo signals, color-codes the first group of contrast enhanced image with a first color, and color-codes the second group of contrast enhanced image with a second color; and a display device which displays the color-coded first group of contrast enhanced image and the color-coded second group of contrast enhanced image. The first number may be greater than the second number.

In one embodiment, the processor may combine the first group of contrast enhanced image and the second group of contrast enhanced image to obtain a combined contrast enhanced image, and the display device may display the combined contrast enhanced image.

In one embodiment, a contrast enhanced ultrasound imaging method is provided, which may include: transmitting unfocused waves to the a target region containing microbubbles in multiple angles; receiving echo signals of the unfocused waves transmitted in the multiple angles; obtaining a first group of contrast enhanced image according to the echo signals, where the first group of contrast enhanced image represents microbubbles with a first velocity; obtaining a second group of contrast enhanced image according to the echo signals, where the second group of contrast enhanced image represents microbubbles with a second velocity and the second velocity is different from the first velocity; displaying the first group of contrast enhanced image with a first color; and displaying the second group of contrast enhanced image with a second color.

In one embodiment, obtaining the first group of contrast enhanced image according to the echo signals may include selecting echo signals corresponding to a first number of angles in the multiple angles from the echo signals to obtain a first group of selected echo signals and generating the first group of contrast enhanced image according to the first group of selected echo signals.

In one embodiment, generating the first group of contrast enhanced image according to the first group of selected echo signals may include performing a coherent compound processing on the first group of selected echo signals, extracting nonlinear signals from the first group of selected echo signals on which the coherent compound processing has been performed and generating the first group of contrast enhanced image according to the nonlinear signals extracted from the first group of selected echo signals on which the coherent compound processing has been performed.

In one embodiment, obtaining the second group of contrast enhanced image according to the echo signals may include selecting echo signals corresponding to a second number of angles in the multiple angles from the echo signals to obtain a second group of selected echo signals and generating the second group of contrast enhanced image according to the second group of selected echo signals.

In one embodiment, generating the second group of contrast enhanced image according to the second group of selected echo signals may include performing a coherent compound processing on the second group of selected echo signals, extracting nonlinear signals from the second group of selected echo signals on which the coherent compound processing has been performed and generating the second group of contrast enhanced image according to the nonlinear signals extracted from the second group of selected echo signals on which the coherent compound processing has been performed.

In one embodiment, an ultrasound imaging system is provided, which may include: a transducer; a transmitting circuit which excites the transducer to transmit unfocused waves to a target region containing microbubbles in multiple angles; a receiving circuit which receives echo signals of the unfocused waves transmitted in the multiple angles; a processor which obtains a first group of contrast enhanced image according to the echo signals and obtains a second group of contrast enhanced image according to the echo signals, where, the first group of contrast enhanced image represents the microbubbles with a first velocity, the second group of contrast enhanced image represents the microbubbles with a second velocity, and the second velocity is different from the first velocity; and a display device which displays the first group of contrast enhanced image with a first color and displays the second group of contrast enhanced image with a second color.

In one embodiment, the processor may select echo signals corresponding to a first number of angles in the multiple angles from the echo signals to obtain a first group of selected echo signals and generate the first group of contrast enhanced image according to the first group of selected echo signals.

In one embodiment, the processor may perform a coherent compound processing on the first group of selected echo signals, extract nonlinear signals from the first group of selected echo signals on which the coherent compound processing has been performed and generate the first group of contrast enhanced image according to the nonlinear signals extracted from the first group of selected echo signals on which the coherent compound processing has been performed.

In one embodiment, the processor may select echo signals corresponding to a second number of angles in the multiple angles from the echo signals to obtain a second group of selected echo signals and generate the second group of contrast enhanced image according to the second group of selected echo signals.

In one embodiment, the processor may perform a coherent compound processing on the second group of selected echo signals, extract nonlinear signals from the second group of selected echo signals on which the coherent compound processing has been performed and generate the second group of contrast enhanced image according to the nonlinear signals extracted from the second group of selected echo signals on which the coherent compound processing has been performed.

In one embodiment, the first color may be different from the second color. Alternatively, the first color and the second color may be a same color and have different transparencies.

In the contrast enhanced ultrasound imaging methods and the ultrasound imaging system of the present disclosure, the echo signals corresponding to different numbers of angles may be selected to obtain the echo signals corresponding to different number of angles, so as to extract the signals representing the microbubbles with different velocities, thereby generating the contrast enhanced images representing the microbubbles with different velocities. Therefore, the contrast microbubbles with different velocities can be easily distinguished.

BRIEF DESCRIPTION OF THE DRAWINGS

In order to more clearly describe the technical solutions in the embodiments of the present disclosure, the drawings of the embodiments will be briefly described below. Obviously, the drawings in the following description are only some embodiments of the present disclosure. Those ordinarily skilled in the art can obtain other drawings based on these drawings without creative work.

DETAILED DESCRIPTION

The technical solutions in the embodiments of the present disclosure will be described clearly and completely in conjunction with the drawings. Obviously, the described embodiments are only a part, but not all, of the embodiments of the present disclosure. Based on the embodiments of the present disclosure, other embodiments may be obtained by those ordinarily skilled in the art without creative efforts, which all fall in the protection scope of the present disclosure.

Figure 5:
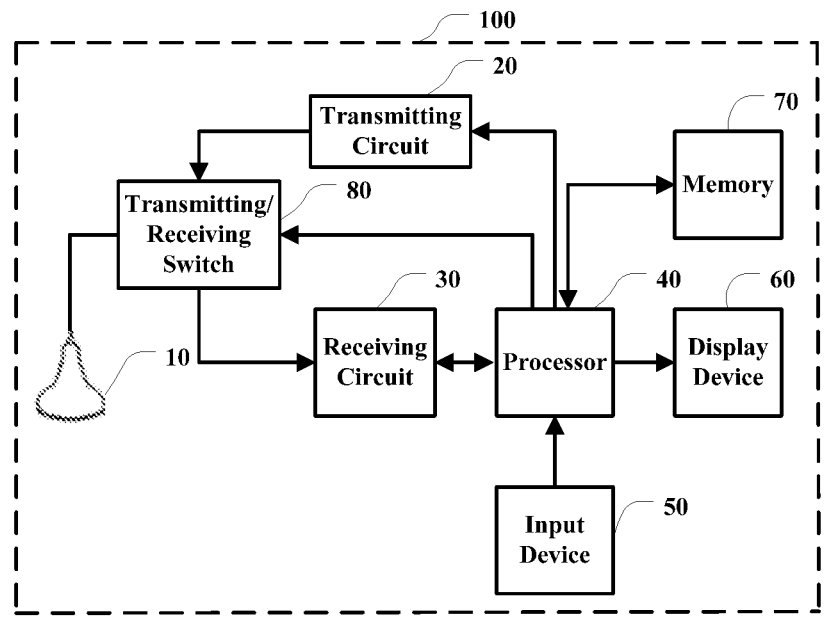
FIG. 5 is a schematic block diagram of an ultrasound imaging system in one embodiment of the present disclosure.

FIG. 5 is a schematic block diagram of an ultrasound imaging system in one embodiment of the present disclosure. Referring to FIG. 5, in some embodiments, the ultrasound imaging system 100 may include a transducer 10, a transmit/receive switch 80, a transmitting circuit 20, a receiving circuit 30, a processor 40, a display device 60, an input device 50, and a memory 70. The transmitting circuit 20 may send a set of pulses to the transducer 10. The transducer 10 may be excited by the pulses to transmit ultrasound waves to the tissue being examined (not shown), and may receive the ultrasound echoes carrying tissue information reflected from the tissue after a certain delay and convert the ultrasound echoes into electrical signals to obtain the ultrasound echo signals. The receiving circuit 30 may receive these ultrasound echo signals, and send them to the processor 40 for subsequent processing. The ultrasound image obtained by the processor 40 may be sent to the display device 60 for display. During this process, the user can input operation instructions or other information through the input device 50. The ultrasound image obtained by the processor 40 may be stored in the memory 70.

In the embodiments of the present disclosure, the contrast enhanced ultrasound imaging methods in the following embodiments may be implemented in the ultrasound imaging system above.

Figure 1:
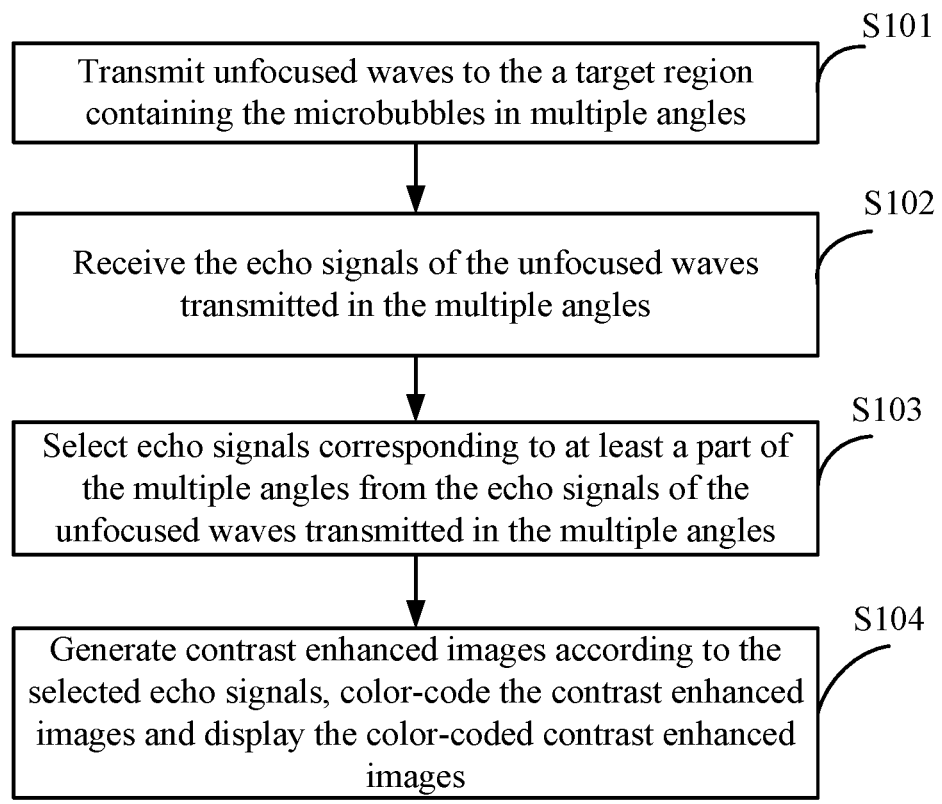
FIG. 1 is a flowchart of a contrast enhanced ultrasound imaging method in one embodiment of the disclosure.

FIG. 1 is a flowchart of a contrast enhanced ultrasound imaging method in one embodiment of the present disclosure. The contrast enhanced ultrasound imaging method may be used to examine an examination portion injected with ultrasound contrast agent. After the ultrasound contrast agent is injected, the examination portion may form a target region containing microbubbles of the contrast agent. In this embodiment, the contrast enhanced ultrasound imaging method may include the following steps.

In step S101, unfocused waves may be transmitted to the target region containing the microbubbles in multiple angles.

Figure 6:
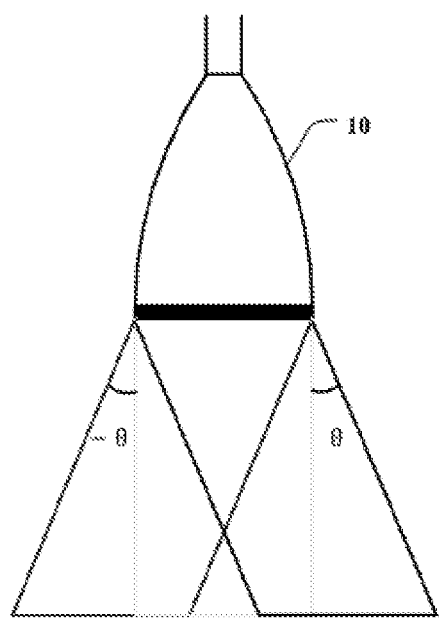
FIG. 6 is a schematic diagram of a transducer transmitting unfocused waves at multiple angles in one embodiment of the present disclosure.

For example, referring to FIGS. 5 and 6, in some embodiments, the transmitting circuit 20 may sequentially excite the transducer 10 to transmit the unfocused waves to the target region (not shown) containing the microbubbles in different angles.

In the present disclosure, the "angle" for transmitting the unfocused waves may be the angle of the propagation direction of the unfocused wave with respect to the plane where the transducers are located. In some embodiments, the "angle" may also be defined in other ways. For example, it may be the angle of the propagation direction of the unfocused wave with respect to the normal of the plane where the transducers are located, (e.g., $\theta$ in FIG. 6), etc.

In some embodiments, when transmitting the unfocused wave in each angle, the transmitting circuit 20 may send two or more transmitting pulses with different amplitudes and phases to the transducer 10, thereby exciting the transducer 10 to transmit multiple unfocused waves to the target region in said angle. The echo signals of these unfocused waves may be received respectively.

In some embodiments, the unfocused wave transmitted may be plane waves. In this case, the wavefront of the ultrasound waves transmitted by the transducers may form a plane to propagate forward. The unfocused plane waves are different from the traditional focused waves which are transmitted line by line along the arrangement direction of the transducers. In theory, the transmitting aperture may include all of the ultrasound transducers, that is, each transmitting may generate one complete frame of ultrasound image. Therefore, with the plane waves, the frame rate of the ultrasound imaging may be greatly increased.

Optionally, the unfocused waves in multiple angles may be preset according to control instructions. For example, the range of the transmitting angle and the number of the transmitting angle may be preset. The range of the transmitting angle may be the angle range of the steering of the unfocused wave transmitting. In the preset range of the transmitting angle, the corresponding number of the transmitting angles may be set, and the ultrasound waves may be sequentially transmitted according to the sequence of the set number of transmitting angles.

In step S102, the echo signals of the unfocused waves transmitted in the multiple angles may be received.

For example, in some embodiments, the receiving circuit 30 may receive or obtain the echo signals of the unfocused waves transmitted in the multiple angles through the transducer 10. These echo signals may be sent to the processor 40 for subsequent processing.

In some embodiments, the processor 40 may select the echo signals corresponding to at least a part of the multiple angles from the echo signals of the unfocused waves transmitted in the multiple angles (S103). Thereafter, the processor 40 may generate a contrast enhanced image according to the selected echo signals, color-code the contrast enhanced image, and display the color-coded contrast enhanced image on the display device 60 (S104).

In the present disclosure, the echo signal "corresponding to" an angle may refer to the echo signal of the unfocused wave transmitted in said angle.

In some embodiments, in step S103, the processor 40 may select echo signals corresponding to a first number of angles from the echo signals of the unfocused waves transmitted in the multiple angles, and select echo signals corresponding to a second number of angles from the echo signals of the unfocused waves transmitted in the multiple angles. Herein, the selected echo signals corresponding to the first number of angles may be referred to as the first group of selected echo signals, and the selected echo signals corresponding to the second number of angles may be referred to as the second group of selected echo signals.

In some embodiments, the number of angles corresponding to the first group of selected echo signals may be different from the number of angles corresponding to the second group of selected echo signals, that is, the first number may be different from the second number. For example, the first number may be greater than the second number.

Figure 2:
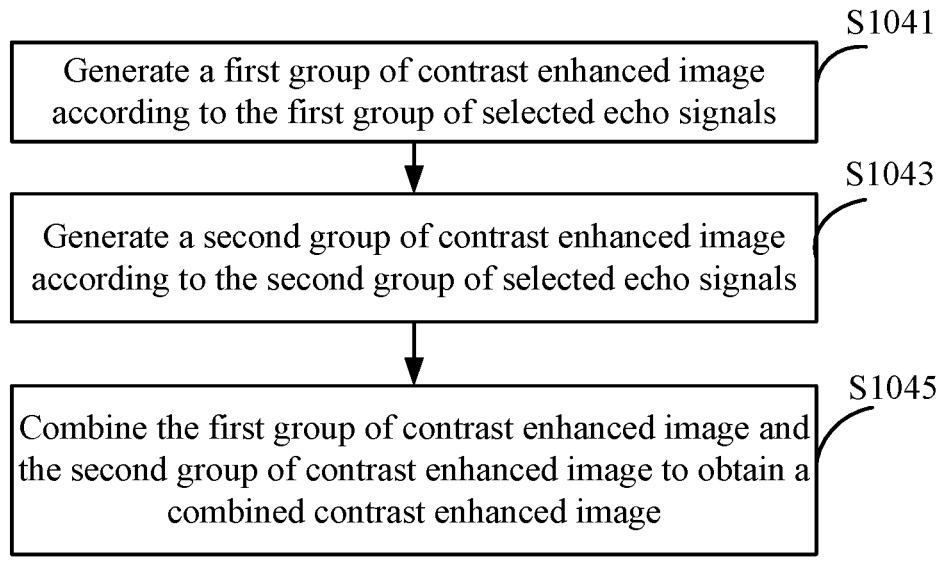
FIG. 2 is a flowchart of step S104 in FIG. 1 in one embodiment.

Correspondingly, in step S104, the processor 40 may generate a first group of contrast enhanced image according to the first group of selected echo signals (FIG. 2, S1041), and generate a second group of contrast enhanced image according to the second group of selected echo signals (FIG. 2, S1043).

For example, in some embodiments, the processor 40 may perform the coherent compound processing on the first group of selected echo signals, and extract the nonlinear signals from the first group of selected echo signals on which the coherent compound processing has been performed. Thereafter, the first group of contrast enhanced image may be generated according to the nonlinear signals extracted from the first group of selected echo signals on which the coherent compound processing has been performed.

Similarly, in some embodiments, the processor 40 may perform the coherent compound processing on the second group of selected echo signals, and extract the nonlinear signals from the second group of selected echo signals on which the coherent compound processing has been performed. Thereafter, the second group of contrast enhanced image may be generated according to the nonlinear signals extracted from the second group of selected echo signals on which the coherent compound processing has been performed.

In ultrasound imaging, assuming that the movement velocity of a target (e.g., the contrast agent microbubbles) is a fixed value, the longer the scanning time, the greater the movement displacement, and the lower the correlation between the correspondingly obtained echo signals of the target. Therefore, when performing the coherent compound on the echo signals in different angles, for the echo signals from the microbubbles with relatively large velocity, the coherent compound may be performed on the echo signals in more angles (the echo signals in more angles mean longer scanning time). After the coherent compound, the intensity of the signals representing the microbubbles with higher velocity will be weakened due to the larger movement displacement, while the intensity of the signals representing the microbubbles with lower velocity will be stronger. Conversely, when the coherent compound is performed on the echo signals in fewer angles (the echo signals in fewer angles mean shorter scanning time), after the coherent compound, the intensity of the signals representing the microbubbles with higher velocity will be stronger. Therefore, when the coherent compound processing is performed on the echo signals in different numbers of angles, the nonlinear signals in the processed echo signals will represent the microbubbles with different velocities. For example, when the coherent compound processing is performed on the echo signals in more angles, the nonlinear signals in the processed echo signals will represent the microbubbles with lower velocity; when the coherent compound processing is performed on the echo signals in fewer angles, the nonlinear signals in the processed echo signals will represent the microbubbles with higher velocity.

As mentioned above, the first number may be different from the second number. That is, compared with the second group of selected echo signals, the first group of selected echo signals includes the echo signals in different number of angles. Therefore, the first group of contrast enhanced image obtained according to the first group of selected echo signals will represent the microbubbles with a first velocity, while the second group of contrast enhanced image obtained according to the second group of selected echo signals will represent the microbubbles with a second velocity which is different from the first velocity.

In some embodiments, as described above, the first number is greater than the second number. That is, compared with the second group of selected echo signals, the first group of selected echo signals includes the echo signals in more angles. Therefore, in these embodiments, the first group of contrast enhanced image obtained according to the first group of selected echo signals will represent the microbubbles with a first velocity which is smaller, while the second group of contrast enhanced image obtained according to the second group of selected echo signals will represent the microbubbles with a second velocity which is larger. That is, in these embodiments, the second velocity is greater than the first velocity.

It can be seen that, in the ultrasound imaging systems or the contrast enhanced ultrasound imaging methods of the embodiments above, the contrast enhanced images of the microbubbles with different velocities can be conveniently obtained, thereby distinguishing microbubbles with different velocities.

In some embodiments, the different groups of contrast enhanced images can be displayed in different ways to facilitate the user to distinguish them. For example, the display device 60 may differently display the first group of contrast enhanced image and the second group of contrast enhanced image.

In some embodiments, colors may be used to differently display the first group of contrast enhanced image and the second group of contrast enhanced image. For example, the processor 40 may color-code the first group of contrast enhanced image and the second group of contrast enhanced image with different colors, and then send them to the display device 60 for display, such that the display device 60 displays the first group of contrast enhanced image and the second group of contrast enhanced image with different colors.

In some embodiments, the processor 40 may color-code the first group of contrast enhanced image with a first color (e.g., red, etc.) and color-code the second group of contrast enhanced image with a second color (e.g., green, etc.), and send the color-coded first group of contrast enhanced image and second group of contrast enhanced image to the display device 60, such that the display device 60 can display the first group of contrast enhanced image with the first color and display the second group of contrast enhanced image with the second color. Here, the first color and the second color may be different. Alternatively, in some embodiments, the first color and the second color may be the same but have different transparency, as long as they can facilitate the user to distinguish the first and second group of contrast enhanced images when viewing.

In other embodiments, other methods may also be used to differently display the first group of contrast enhanced image and the second group of contrast enhanced image. For example, different markers (for example, different geometric shapes, different transparency, different image contour markers, etc.) may be used to display the first group of contrast enhanced image and the second group of contrast enhanced image, such that the user can easily distinguish them.

The embodiments in which two groups of contrast enhanced image are obtained have been described above. It can be easily understood that, in other embodiments, similar methods may also be used to obtain more groups of contrast enhanced images representing the contrast microbubbles with different velocities and these groups of contrast enhanced images may be displayed differently.

Therefore, by displaying the contrast enhanced images representing the microbubbles with different velocities in different ways, the user can conveniently distinguish different groups of contrast enhanced images representing the microbubbles with different velocities when viewing the contrast enhanced images.

In some embodiments, after obtaining the first group of contrast enhanced image and the second group of contrast enhanced image, the first group of contrast enhanced image and the second group of contrast enhanced image may be combined to obtain a combined contrast enhanced image (see FIG. 2, S1045). For example, in some embodiments, the first group of contrast enhanced image and the second group of contrast enhanced image may be weighted and summed to obtain the combined contrast enhanced image. Thereafter, the combined contrast enhanced image may be sent to the display device 60 for display.

In some embodiments, after the step S104, the processor 40 may also receive (for example, through the input device 50) an adjustment instruction for adjusting the color transparency of the microbubble area, and adjust the transparencies of the colors of the microbubble areas in the first group of contrast enhanced image and the second group of contrast enhanced image according to the adjustment instruction, such that the transparencies of the colors of the microbubble areas in the first group of contrast enhanced image and the second group of contrast enhanced image are different. For example, at least one of the first group of contrast enhanced image and the second group of contrast enhanced image may be highlighted. For example, the user can adjust the proportion of different colors. For example, if it is desired to focus on the area of fast microbubbles, the user can change the transparencies of the colors corresponding to different velocities by adjusting the menu on the interface or the knob on the device so as to highlight the area where the fast moving microbubbles are located in the contrast enhanced image.

Specifically, the color transparency of the first group of contrast enhanced image or the second group of contrast enhanced image that needs to be highlighted can be reduced and the color transparency of the first group of contrast enhanced image or the second group of contrast enhanced image that does not need to be highlighted may be increased according to the adjustment instruction, such that the first group of contrast enhanced image or the second group of contrast enhanced image that needs to be highlighted is highlighted and can be highlighted on the ultrasound B-mode image.

In some embodiments, after the step S104, the processor 40 may also display the combined contrast enhanced image obtained according to the first group of contrast enhanced image and the second group of contrast enhanced image and the obtained ultrasound B-mode image on different display windows of the display device 60. Alternatively, the processor 40 may display the obtained ultrasound B-mode image and the combined contrast enhanced image on the same display window. The ultrasound B-mode image may be an ultrasound grayscale image. The ultrasound B-mode image may be obtained according to the echo signals derived from the same unfocused waves as the first group of contrast enhanced image and the second group of contrast enhanced image but through different processing. Alternatively, the ultrasound B-mode image may be obtained by separate transmitting of focused waves, receiving and the corresponding signal processing process.

Figure 3:
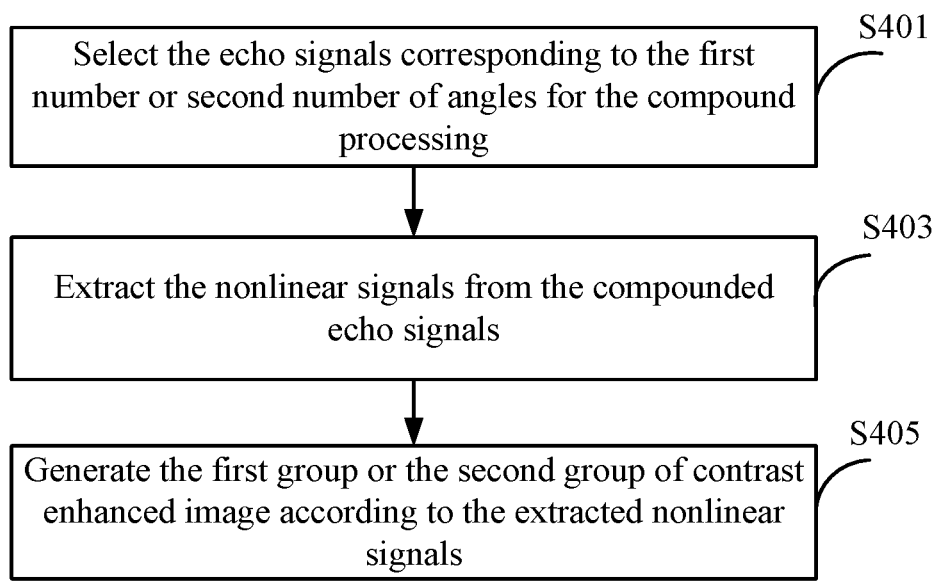
FIG. 3 is a flowchart of a method for generating a contrast enhanced image used in FIG. 1 or FIG. 3 in one embodiment of the present disclosure.

FIG. 3 shows a specific example of generating the first group of contrast enhanced image or the second group of contrast enhanced image by the coherent compound processing in one embodiment of the present disclosure. With reference to the embodiments in FIG. 1, the process may include the following steps.

In step S401, the processor 40 may select the echo signals corresponding to the first number or second number of angles for the compound processing.

In the contrast enhanced imaging, in each angle, the transmitting circuit 20 may send at least three pulses with different amplitudes to the transducers to excite the transducers to transmit at least three unfocused waves to the target region. The echoes of the at least three unfocused waves in said angle may be received to obtain the echo signals in said angle. The amplitude weights of the at least three pulses with different amplitudes may be a, 1 and 1-a, respectively, where a represents the amplitude weight of the pulse transmitted in the current angle.

Correspondingly, in step S401, the processor 40 may perform a coherent average one the echo signals in the various angles in the first group of selected echo signals (or the second group of selected echo signals) one by one to obtain a compounded signals. The weight of the compounded echo signals may be $$\frac{1}{N}\sum_{i=1}^{N} a_i, 1, \frac{1}{N}\sum_{i=1}^{N}(1-a_i),$$

respectively, where i represents the angle index, i=1, 2 ... N, and N is the number of the angles corresponding to the first group of selected echo signals (or the second group of selected echo signal), i.e. the first number (or the second number).

The processor 40 may perform weighting processing on the compounded echo signals with different coefficients to extract the nonlinear signals therein (S403). For example, in some embodiments, the processor 40 may sum the echo signals with the weights of $$\frac{1}{N}\sum_{i=1}^{N} a_i \text{ and } \frac{1}{N}\sum_{i=1}^{N}(1-a_i)$$

to obtain the first summed echo signals, perform the splicing modulation on the first summed echo signals and the echo signals with the weight of 1 to obtain the modulated echo signals, and extract the nonlinear signals from the modulated echo signals with a low-pass filter.

Thereafter, the processor 40 may perform subsequent processing on the extracted nonlinear signals to generate the first group of contrast enhanced image (or the second group of contrast enhanced image) (S405). For example, in some embodiments, the processor 40 may perform at least demodulation, filtering, envelope detection and logarithmic compression, etc. on the extracted nonlinear signals to obtain the first group of contrast enhanced image or the second group of contrast enhanced image based on the echo signal in the first number or second number of angles.

In some embodiments, the angle range and the number of angles of the unfocused waves may be preset. For example, the angle range may be set to [−10°, 10°], and the number of the angles within a scanning range of 20 degrees may be 61. The specific values may be set according to clinical needs, which will not be limited herein. For example, the first number may be 61, that is, the echo signals in all angles may be selected as the first group of selected echo signals for generating the first group of contrast enhanced image. The second number may be 9, that is, the echo signals in 9 of the 61 angles may be selected as the second group of selected echo signals for generating the second group of contrast enhanced image. The two groups of images can be weighted and summed to generate the combined contrast enhanced image. Although several specific values are listed here, those skilled in the art should understand that the angle range, the number of the angles, the specific value of the first number and the specific value of the second number may be determined according to actual needs, but not limited to the specific values used as examples above. For example, the first number may be different from the preset number of angles in the preset angle range, and the echo signals in all angles may not be selected as the first group of selected echo signals, and so on.

With the methods above, the signals representing the microbubbles with different velocities may be extracted through the compound processing on the echo signals in different number of angles, and the ultrasound contrast enhanced image may be generated accordingly, thereby effectively representing the difference in the velocities of the microbubbles (i.e. the blood flow).

Figure 4:
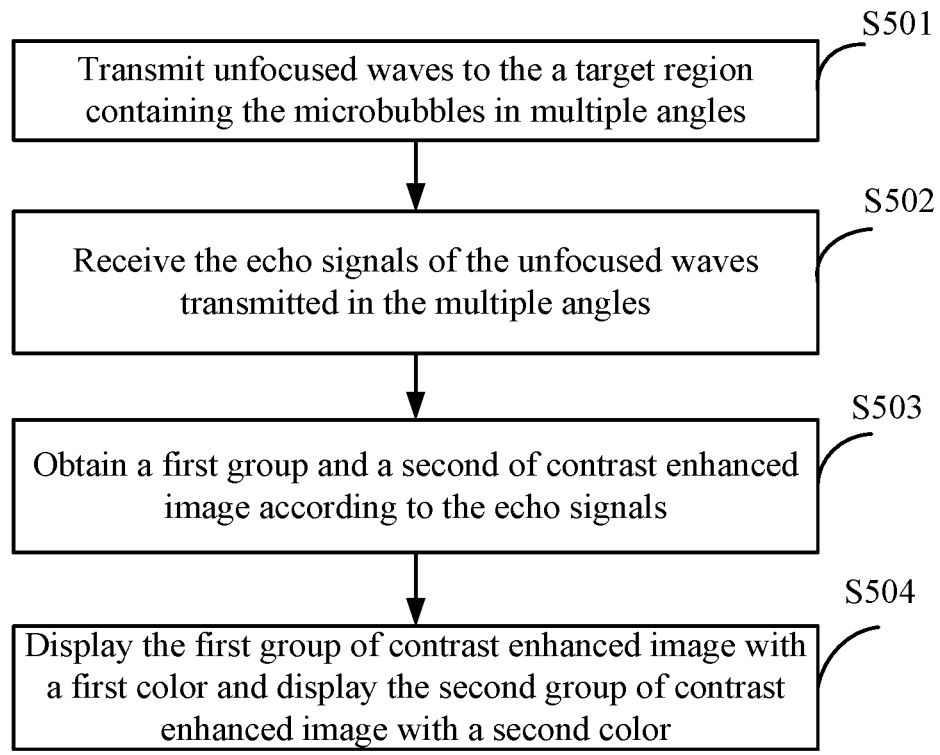
FIG. 4 is a flowchart of a contrast enhanced ultrasound imaging method in one embodiment of the present disclosure.

FIG. 4 shows a flowchart of an method for displaying the ultrasound contrast enhanced image in one embodiment of the present disclosure. The method may include the following steps.

In step S501, the transmitting circuit 20 may excite the transducer 10 to transmit unfocused waves to the target region containing microbubbles in multiple angles.

In step S502, the receiving circuit 30 may receive the echo signals of the unfocused waves transmitted in the multiple angles.

In step S503, the processor 40 may obtain the first group of contrast enhanced image and the second group of contrast enhanced image according to the echo signals. The first group of contrast enhanced image represents the microbubbles having the first velocity, and the second group of contrast enhanced image represents the microbubbles having the second velocity. The second velocity is different from the first velocity.

In step S504, the display device 60 may display the first group of contrast enhanced image with the first color and display the second group of contrast enhanced image with the second color.

In this embodiment, the processor 40 may select the echo signals corresponding to the first number of angles of the multiple angles from the echo signals obtained in step S502 to obtain the first group of selected echo signals, and generate the first group of contrast enhanced image according to the first group of selected echo signals. For example, the processor 40 may perform the coherent compound processing on the first group of selected echo signals, extract the nonlinear signals from the first group of selected echo signals on which the coherent compound processing has been performed, and generate the first group of contrast enhanced image according to the nonlinear signals extracted from the first group of selected echo signals on which the coherent compound processing has been performed.

Similarly, in this embodiment, the processor 40 may select the echo signals corresponding to the second number of angles of the multiple angles from the echo signals obtained in step S502 to obtain the second group of selected echo signals, and generate the second group of contrast enhanced image according to the second group of selected echo signals. For example, the processor 40 may perform the coherent compound processing on the second group of selected echo signals, extract the nonlinear signals from the second group of selected echo signals on which the coherent compound processing has been performed, and generate the second group of contrast enhanced image according to the nonlinear signals extracted from the second group of selected echo signals on which the coherent compound processing has been performed.

In this embodiment, the first color and second color may be different. Alternatively, the first color and second color may be the same but have different transparencies.

In the embodiments of the present disclosure, the input device 50 of the ultrasound imaging system may be a mouse, a touchpad, a touchscreen, or the like.

In the embodiments of the present disclosure, the display device 60 of the ultrasound imaging system may be a touch display screen, a liquid crystal display screen, etc. Alternatively, the display device 60 may be a separate display device independent of the ultrasound imaging system 100, such as a liquid crystal display, a television, etc. Alternatively, the display device 60 may also be the display screen of an electronic device such as a mobile phone or a tablet computer, etc.

In the embodiments of the present disclosure, the memory 70 of the ultrasound imaging system may be a flash memory card, a solid-state memory, a hard disk, or the like.

In one embodiment of the present disclosure, a computer readable storage medium is provided. The computer readable storage medium may store multiple program instructions. After the multiple program instructions are executed by the processor 40, some or all of the steps, or any combination thereof, in the contrast enhanced ultrasound imaging methods in the embodiments above may be implemented.

In some embodiments, the computer readable storage medium may be the memory 70, which may be a non-volatile storage medium such as a flash memory card, a solid state memory, a hard disk or the like.

In the embodiments of the present disclosure, the processor 40 of the ultrasound imaging system may be implemented by software, hardware, firmware, or a combination thereof. The processor 40 may use circuits, one or more application specific integrated circuits (ASIC), one or more universal integrated circuits, one or more microprocessors, one or more programmable logic devices, or a combination of the circuits or devices above, or other suitable circuits or devices, such that the processor 40 can perform the steps in the contrast enhanced ultrasound imaging methods in the embodiments above.

In the contrast enhanced ultrasound imaging methods and the ultrasound imaging system of the present disclosure, the echo signals corresponding to different numbers of angles may be selected to obtain the echo signals corresponding to different number of angles, so as to extract the signals representing the microbubbles with different velocities, thereby generating the contrast enhanced images representing the microbubbles with different velocities. Therefore, the contrast microbubbles with different velocities can be easily distinguished.

The embodiments of the present disclosure have been described above. It should be noted that many improvements and modifications may be made by those ordinarily skilled in the art without departing from the concepts of the present disclosure, which all shall fall in the protection scope of the present disclosure.

The invention claimed is:
1. An ultrasound imaging system, comprising:
a transducer;
a transmitting circuit which excites the transducer to transmit unfocused waves to a target region containing microbubbles in multiple angles;
a receiving circuit which receives echo signals of the unfocused waves transmitted in the multiple angles through the transducer;
a processor which:
  selects a group of echo signals corresponding to a first number of angles in the multiple angles from the received echo signals of the unfocused waves transmitted in the multiple angles to obtain a first group of selected echo signals;
  selects a different group of echo signals corresponding to a second number of angles in the multiple angles from the received echo signals of the unfocused waves transmitted in the multiple angles to obtain a second group of selected echo signals;
  generates, according to the first group of selected echo signals, a first group of contrast enhanced images comprising a first intensity of signal representing a first group of microbubbles and a second intensity of signal representing a second group of microbubbles, wherein the second group of microbubbles has a lower velocity than the first group of microbubbles; and
  generates, according to the second group of selected echo signals, a second group of contrast enhanced images comprising a third intensity of signal representing the first group of microbubbles and a fourth intensity of signal representing the second group of microbubbles, wherein the first intensity is weaker than the third intensity, and the fourth intensity is weaker than the second intensity; and
a display device which differently displays the first group of contrast enhanced images and the second group of contrast enhanced images or displays a combined contrast enhanced image based at least on the first group of contrast enhanced images and the second group of contrast enhanced images;
wherein the first number is greater than the second number.

2. The system of claim 1, wherein the unfocused waves are plane waves.

3. The system of claim 1, wherein, the processor combines the first group of contrast enhanced images and the second group of contrast enhanced images to obtain the combined contrast enhanced image.

4. The system of claim 1, wherein:
the first group of contrast enhanced images is generated according to the first group of selected echo signals by:
  performing a coherent compound processing on the first group of selected echo signals;
  extracting nonlinear signals from the first group of selected echo signals on which the coherent compound processing has been performed; and
  generating the first group of contrast enhanced images according to the nonlinear signals extracted from the first group of selected echo signals on which the coherent compound processing has been performed; and
the second group of contrast enhanced images is generated according to the second group of selected echo signals by:

performing a coherent compound processing on the second group of selected echo signals;

extracting nonlinear signals from the second group of selected echo signals on which the coherent compound processing has been performed; and generating the second group of contrast enhanced images according to the nonlinear signals extracted from the second group of selected echo signals on which the coherent compound processing has been performed.

5. The system of claim 1, wherein:

the first group of contrast enhanced images is color coded with a first color, and the second group of contrast enhanced images is color coded with a second color.

6. The system of claim 5, wherein the first color is different from the second color.

7. An ultrasound imaging method, comprising:

transmitting unfocused waves to a target region containing microbubbles in multiple angles;

receiving echo signals of the unfocused waves transmitted in the multiple angles;

selecting a group of echo signals corresponding to a first number of angles in the multiple angles from the received echo signals to obtain a first group of selected echo signals;

selecting a different group of echo signals corresponding to a second number of angles in the multiple angles from the received echo signals to obtain a second group of selected echo signals, wherein the first number is greater than the second number;

generating, according to the first group of selected echo signals, a first group of contrast enhanced images comprising a first intensity of signal representing a first group of microbubbles and a second intensity of signal representing a second group of microbubbles, wherein the second group of microbubbles has a lower velocity than the first group of microbubbles;

generating, according to the second group of selected echo signals, a second group of contrast enhanced images comprising a third intensity of signal representing the first group of microbubbles and a fourth intensity of signal representing the second group of microbubbles, wherein the first intensity is weaker than the third intensity, and the fourth intensity is weaker than the second intensity; and displaying the first group of contrast enhanced images and the second group of contrast enhanced images differently or a combined contrast enhanced image based at least on the first group of contrast enhanced images and the second group of contrast enhanced images.

8. The method of claim 7, wherein generating the first group of contrast enhanced images comprises:

performing a coherent compound processing on the first group of selected echo signals to generate the first group of contrast enhanced images.

9. The method of claim 7, wherein generating the second group of contrast enhanced images comprises:

performing a coherent compound processing on the second group of selected echo signals to generate the second group of contrast enhanced images.

10. The method of claim 7, further comprising:

generating a B-mode image based on the echo signals, wherein the combined contrast enhanced image based at least on the first group of contrast enhanced images and the second group of contrast enhanced images is based at least on the first group of contrast enhanced images, the second group of contrast enhanced images, and the B-mode image.

11. The method of claim 7, wherein displaying the first group of contrast enhanced images and the second group of contrast enhanced images differently comprises displaying the first group of contrast enhanced images and the second group of contrast enhanced images in different colors or in different transparencies of a same color.

12. An ultrasound imaging system, comprising:

a transducer;

a transmitting circuit which excites the transducer to transmit unfocused waves to a target region containing microbubbles in multiple angles;

a receiving circuit which receives echo signals of the unfocused waves transmitted in the multiple angles through the transducer;

a processor which:

selects echo signals corresponding to a first number of angles in the multiple angles from the echo signals of the unfocused waves transmitted in the multiple angles to obtain a first group of selected echo signals;

selects echo signals corresponding to a second number of angles in the multiple angles from the echo signals of the unfocused waves transmitted in the multiple angles to obtain a second group of selected echo signals;

generates, according to the first group of selected echo signals, a first group of contrast enhanced images comprising a first intensity of signal representing a first group of microbubbles and a second intensity of signal representing a second group of microbubbles, wherein the second group of microbubbles has a lower velocity than the first group of microbubbles; and generates, according to the second group of selected echo signals, a second group of contrast enhanced images comprising a third intensity of signal representing the first group of microbubbles and a fourth intensity of signal representing the second group of microbubbles, wherein the first intensity is weaker than the third intensity, and the fourth intensity is weaker than the second intensity; and a display device which differently displays the first group of contrast enhanced images and the second group of contrast enhanced images or displays a combined contrast enhanced image based on the first group of contrast enhanced images and the second group of contrast enhanced images;

wherein the first number is greater than the second number.

13. The ultrasound imaging system of claim 12, wherein to generate the first group of contrast enhanced images, the processor:

performs a coherent compound processing on the first group of selected echo signals.

14. The ultrasound imaging system of claim 12, wherein to generate the second group of contrast enhanced images, the processor:

performs a coherent compound processing on the second group of selected echo signals.

15. The ultrasound imaging system of claim 12, wherein:

the processor generates a B-mode image based on the echo signals, wherein the combined contrast enhanced image based at least on the first group of contrast enhanced images and the second group of contrast enhanced images is based at least on the first group of contrast enhanced images, the second group of contrast enhanced images, and the B-mode image.

\* \* \* \* \*